US00PP19924P2

(12) United States Plant Patent
Rowe, III

(10) Patent No.: US PP19,924 P2
(45) Date of Patent: Apr. 14, 2009

(54) BOXWOOD PLANT NAMED 'CONROWE'

(50) Latin Name: *Buxus sempervirens*
Varietal Denomination: Conrowe

(75) Inventor: Gordon D. Rowe, III, Unionville, PA (US)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 11/984,515

(22) Filed: Nov. 19, 2007

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
*Assistant Examiner*—June Hwu
(74) *Attorney, Agent, or Firm*—Buchanan Ingersoll & Rooney PC

(57) ABSTRACT

A new and distinct Boxwood plant is provided which originated as a limb mutation of the 'Green Velvet' cultivar (non-patented in the United States). The new cultivar readily can be distinguished from the 'Green Velvet' cultivar in view of its significantly larger leaf size. The growth habit is dense, mounded and compact. Attractive deep olive green foliage is formed which well retains its coloration throughout the year in the absence of any substantial color change during the winter. Excellent winter hardiness to at least U.S.D.A. Hardiness Zone No. 5 is displayed. The plant is well suited for consistently providing attractive ornamentation in the landscape.

1 Drawing Sheet

Botanical/commercial classification: *Buxus sempervirens*/ Boxwood Plant.
Varietal denomination: cv. Conrowe.

SUMMARY OF THE INVENTION

The new Boxwood plant of the present invention was discovered during January 1998 at West Grove, Pa., U.S.A., while growing in a plant nursery among vegetatively propagated plants of the 'Green Velvet' cultivar (non-patented in the United States). The new cultivar of the present invention is a limb mutation of the 'Green Velvet' cultivar of unknown causation. I was attracted to the distinctive appearance of the limb primarily because of its larger leaf size combined with other attractive characteristics. Had I not discovered and preserved this mutation, it would have been lost to mankind.

The new cultivar has been carefully preserved and has been evaluated to confirm that its characteristics are reliably expressed.

It has been found that the new Boxwood plant of the present invention displays the following combination of characteristics:

(a) forms a dense, mounded and compact growth habit, (b) forms attractive deep olive green foliage throughout the year in the absence of any substantial color change during the winter, (c) exhibits excellent winter hardiness to at least U.S.D.A. Hardiness Zone No. 5, and (d) exhibits a larger leaf size than the 'Green Velvet' cultivar (non-patented in the United States).

The new evergreen cultivar of the present invention well retains its attractive appearance throughout the year. The deep olive green coloration of the foliage is well maintained even during the winter, unlike many previously available Boxwood cultivars which tend to assume a brownish-green foliage coloration during the winter. The new cultivar also exhibits good resistance to winter burn. The hardiness of the new cultivar during observations to date has been found to be at least equal to or to exceed most previously known Boxwood cultivars that are known for their superior hardiness.

The new cultivar of the present invention can be grown to advantage as attractive ornamentation in the landscape, and is particularly well suited for use in the formation of low-growing hedges or in edge plantings. The new plant has been found to perform well in the sun as well as in the shade while growing in many soil types, including those which contain clay. Some pruning may be desired to maintain the compact and mounded growth habit of the new cultivar.

The new cultivar of the present invention can be readily distinguished from the 'Green Velvet' cultivar in view of the larger leaf size.

Asexual reproduction of the new cultivar by the use of cuttings has been carried out at West Grove, Pa., U.S.A. Such propagation has confirmed that the unique combination of characteristics of the new cultivar has been stably established and is well transmitted to successive generations. The new cultivar asexually reproduces in a true-to-type manner.

The new cultivar has been named 'Conrowe' and will be marketed under the GORDO trademark.

BRIEF DESCRIPTION OF THE PHOTOGRAPH

The accompanying photograph shows as nearly true as it is reasonably possible to make the same in a color illustration of this character, a typical specimen of the new variety. A mature plant at an age of approximately six years is shown while growing outdoors in a container in full sun during July 2005 at West Grove, Pa., U.S.A. The dense, mounded and compact growth habit, larger leaves and attractive deep olive green foliage coloration are illustrated.

DETAILED DESCRIPTION

The following is a detailed description of the new cultivar of the present invention which was prepared while observing five-year-old plants growing in containers outdoors during September 2007 at West Grove, Pa., U.S.A. Color terminology is in accordance with the R.H.S. Colour Chart of The Royal Horticultural Society, London, England, except when general color terms which are to be accorded their customary dictionary significance are used.

Type: Hardy broad-leafed evergreen shrub for garden decoration and general landscape usage.

Plant:

*Growth habit.*—Dense, mounded, and compact.

*Growth rate.*—Medium growing and somewhat slower than most other *Buxus sempervirens* cultivars.

*Height.*—Approximately 2.5 feet at an age of five years. A fully mature plant commonly assumes a height of approximately six feet.

*Width.*—Approximately 2.5 feet at an age of five years. A fully mature plant commonly assumes a width of approximately six feet.

*Juvenile branches.*—Diameter: commonly approximately 0.25 cm on average. Texture: smooth. Color: Yellow-Green Group 144B with striations of Green Group 143B.

*Mature branches.*—Diameter: commonly approximately 0.7 cm on average. Texture: somewhat rough. Color: Yellow-Green Group 143C with striations of Greyed-Orange Group 164C.

Foliage:

*Juvenile foliage.*—Length: commonly approximately 2.3 cm on average. This compares to a length of approximately 2 cm for the 'Green Velvet' cultivar. Width: commonly approximately 1.7 cm on average. This compares to a width of approximately 1.2 cm for the 'Green Velvet' cultivar. Shape: ovate. Apex: notched. Margin: entire. Color of upper surface: Green Group 139A. Color of under surface: Yellow-Green Group 144A with a margin of Green Group 137A and a midrib of Yellow-Green Group 145A. Fragrance: typical boxwood scent.

*Mature foliage.*—Length: commonly approximately 2.5 cm on average. This compares to a length of approximately 1.5 cm for the 'Green Velvet' cultivar. Width: commonly approximately 2.2 cm on average. This compares to a width of approximately 1.1 cm for the 'Green Velvet' cultivar. Shape: substantially round. Apex: notched. Texture: glossy on the upper surface, and smooth with ridges on the under surface. Margin: entire. Color of upper surface: commonly near Green Group 137A and Green Group 139A. Color of lower surface: Yellow-Green Group 144A and 144B with a midrib of Yellow-Green Group 145C. Fragrance: typical boxwood scent.

*Petioles.*—Length: approximately 0.25 cm on average when mature. Diameter: approximately 1 mm on average when mature. Texture: surface is smooth when mature. Color: Yellow-Green Group 144B with striations of Green Group 143B.

Inflorescence:

*Time.*—Flowering commonly occurs in March to April.

*Type.*—Apetalous in axilliary or terminal clusters consisting of a terminal pistillate flower and several staminate flowers.

*Fruit.*—Three-celled capsule with each being valve two-horned, approximately 6 mm in diameter, and near Greyed-Orange Group 165D in coloration.

*Seeds.*—Shining black.

Development:

*Hardiness.*—To at least U.S.D.A. Hardiness Zone No. 5. Grows well in U.S.D.A. Hardiness Zone Nos. 5 to 9.

*Disease resistance.*—No disease problems have been observed during observations to date.

*Insect tolerance.*—No insect damage has been observed during observations to date.

I claim:

1. A new and distinct Boxwood plant possessing the following characteristics:

(a) forms a dense, mounded and compact growth habit, (b) forms attractive deep olive green foliage throughout the year in the absence of any substantial color change during the winter, (c) exhibits excellent winter hardiness to at least U.S.D.A. Hardiness Zone No. 5, and (d) exhibits a larger leaf size than the 'Green Velvet' cultivar (non-patented in the United States);

substantially as illustrated and described.

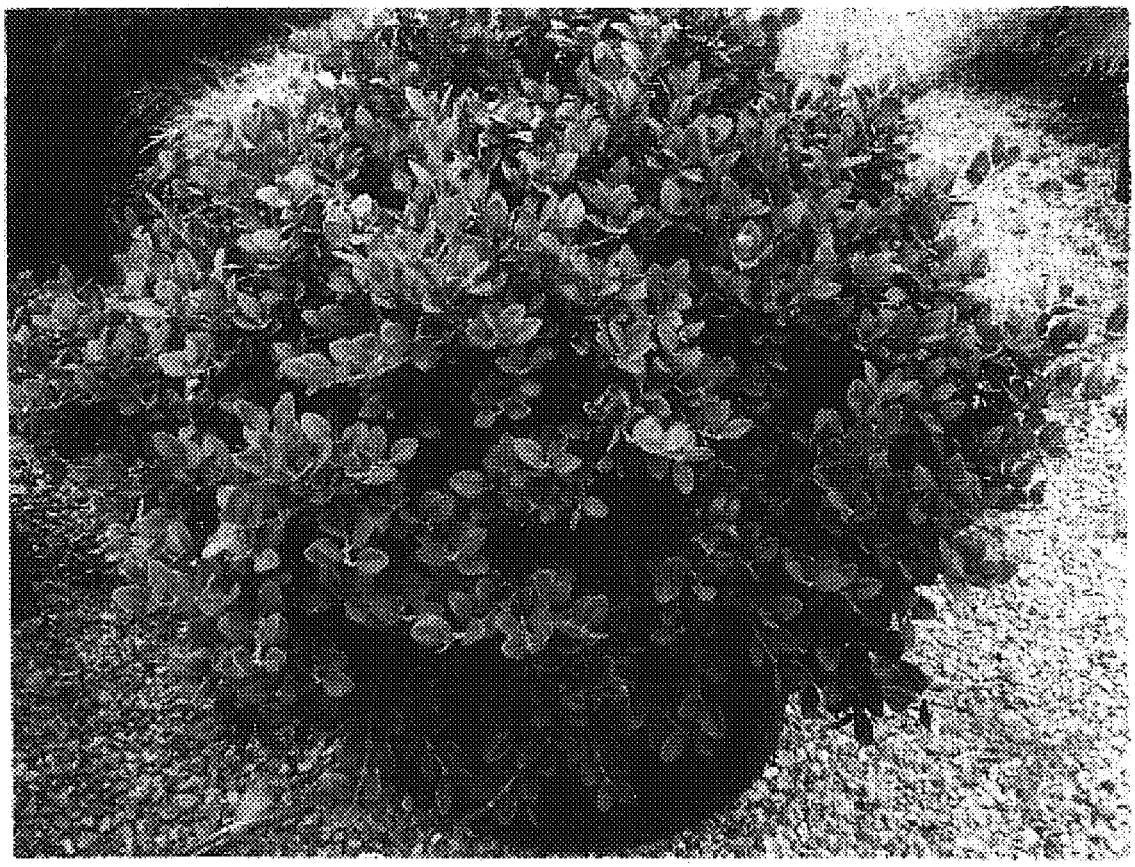

* * * * *